(12) United States Patent
Baer (10) Patent No.: US 7,816,654 B2
(45) Date of Patent: Oct. 19, 2010

(54) SINGLE WAVELENGTH STIMULATED EMISSION DEPLETION MICROSCOPY

(76) Inventor: Stephen C. Baer, 10 Poplar Rd., Cambridge, MA (US) 02138

( * ) Notice: Subject to any disclaimer, the term of this patent is extended or adjusted under 35 U.S.C. 154(b) by 90 days.

(21) Appl. No.: 11/795,094

(22) PCT Filed: Jan. 17, 2006

(86) PCT No.: PCT/US2006/001961
§ 371 (c)(1),
(2), (4) Date: Mar. 17, 2008

(87) PCT Pub. No.: WO2006/078857
PCT Pub. Date: Jul. 27, 2006

(65) Prior Publication Data
US 2009/0121153 A1    May 14, 2009

Related U.S. Application Data (60) Provisional application No. 60/644,597, filed on Jan. 16, 2005, provisional application No. 60/644,629, filed on Jan. 16, 2005, provisional application No. 60/669,302, filed on Apr. 6, 2005.

(51) Int. Cl.
G01J 1/58 (2006.01)
(52) U.S. Cl. .................................. 250/458.1
(58) Field of Classification Search .............. 250/459.1, 250/492.1
See application file for complete search history.

(56) References Cited

U.S. PATENT DOCUMENTS

| | | | |
|---|---|---|---|
| 3,705,755 A | 12/1972 | Baer | |
| 5,034,613 A | 7/1991 | Denk et al. | |
| 5,731,588 A | 3/1998 | Hell et al. | |
| 5,777,342 A | 7/1998 | Baer | |
| 5,866,911 A | 2/1999 | Baer | |
| 5,952,668 A | 9/1999 | Baer | |
| 6,178,041 B1 | 1/2001 | Simon | |
| 6,259,104 B1 | 7/2001 | Baer | |
| 7,064,824 B2 | 6/2006 | Hell | |
| 2004/0212799 A1 | 10/2004 | Hell | |
| 2004/0223385 A1* | 11/2004 | Fleming et al. | ............. 365/202 |

OTHER PUBLICATIONS

Hell, S.W., et al.; "Breaking the diffraction resolution limit by stimulated emission: stimulated-emission-depletion fluorescence microscopy";Optics Letter 1994;19(11):780-782.

Hell, S.W., et al.; "Ground-state-depletion fluorescence microscopy: a concept for breaking the diffraction resolution limit"; Applied Physics B 1995;60:495-497.

(Continued)

Primary Examiner—David P Porta
Assistant Examiner—Marcus H Taningco (57) ABSTRACT

In apparatus for superresolution microscopy or microlithography, wherein a spot in the specimen to be examined or in the microlithographic medium is raised to an excited state by a first pulse of light, and a second pulse of light reduces the excitation in the peripheral parts of the spot to increase the resolution of the instrument, a method whereby the wavelength of the second pulse in the specimen or medium is the same as the wavelength of the first pulse, thereby allowing the cost and complexity of the apparatus to be lowered.

23 Claims, 5 Drawing Sheets

OTHER PUBLICATIONS

Heintzmann, Rainer, et al.; "Saturated patterned excitation microscopy-a concept for optical resolution improvement"; J. Opt. Soc. Am. A 2002; 19(8):1599-1609.

Hell, Stefan W.; "Toward fluorescence nanoscopy"; Nature Biotechnology 2003; 21 (11):1347-1355.

Hell, S.W., et al.; "Imaging and writing at the nanoscale with focused visible light through saturable optical transitions"; Applied Physics A 2003; 77:859-860.

Hell, Stefan W.; "Strategy for far-field optical imaging and writing without diffraction limit"; Physics Letters A 2004; 326:140-145.

Dyba et al., Photostability of a fluorescent marker under pulsed excited-state depletion through stimulated emission, Appl.Opt., 2003, p. 5123-5129, vol. 42, Opt.Soc.Am., US.

Zhou et al., An efficient two-photon-generated photoacid applied to positive-tone 3D microfabrication, Science, 2002, p. 1106-1109, vol. 296, AAAS, US.

* cited by examiner

SINGLE WAVELENGTH STIMULATED EMISSION DEPLETION MICROSCOPY

CROSS REFERENCE TO RELATED APPLICATION

This application claims priority from U.S. Provisional Patent Application Ser. No. 60/644,597, filed Jan. 16, 2005, from U.S. Provisional Patent Application Ser. No. 60/644,629, filed Jan. 16, 2005 and from U.S. Provisional Patent Application Ser. No. 60/669,302, filed Apr. 6, 2005, the entire disclosure of which is hereby incorporated by reference.

FIELD OF THE INVENTION

The present invention relates to imaging apparatus, and more specifically to fluorescence microscopes and microlithography exposure tools that resolve detail finer than the Abbe resolution limit. Still more specifically, the present invention relates to improvements in devices, such as stimulated emission depletion microscopy and microlithography exposure tools, which scan a specimen or microlithographic emulsion with a spot or line at a first wavelength, and by means of radiation at a second wavelength, reduce the excitation in the peripheral parts of the spot or line, thereby improving the resolution of the instrument.

BACKGROUND OF THE INVENTION

Hell and Wichmann in U.S. Pat. No. 5,731,588 and Baer in U.S. Pat. Nos. 5,777,342, 5,866,911, 5,952,668 and 6,259,104 proposed using stimulated emission to quench excitation in the peripheral parts of an excited spot in a scanning fluorescence microscope to improve resolution. In this method a spot was excited by a light pulse of one wavelength (the excitation wavelength) and quenched by a subsequent light pulse of a second wavelength (the quenching wavelength). The technique is often referred to as "STED" for "stimulated emission depletion" microscopy. This method has been experimentally verified as published in various papers from the laboratory of Stefan Hell.

Other techniques related to STED have been proposed that do not involve stimulated emission, but share with STED the need for providing an exciting beam to the specimen paired with a second bean to reduce excitation in the peripheral parts of the excited spot or line, thereby "sculpting" the excited spot or line to have a sharper central maximum. An example of such alternative techniques, which will be referred to herein as "STED-like," is excited state depletion microscopy (Hell and Kroug, Appl. Phys. B. 60:495(95)), where the sculpting beam pulse occurs before the excitation pulse and renders molecules exposed to the sculpting beam temporarily insensitive to subsequent excitation by the excitation beam. Furthermore, various STED-like techniques have been proposed that employ proteins and dye molecules able to switch between a fluorescent and non-fluorescent forms by light pulses of appropriate wavelengths.

Although these STED and STED-like techniques promise greatly improved resolution, the requirement of providing two extremely short pulses of different wavelengths in the specimen, such that the pulses are synchronized with each other, has impeded the acceptance of the technique as a practical route to superresolution. Although various proposals have been made to create two synchronized pulsed output beams with different wavelengths from a single input laser (eg., U.S. Pat. No. 5,866,911), such proposals require some frequency converting devices such as frequency multiplying crystals or optical parametric oscillators to convert the wavelength of one or both of these beams, so that even though the two beams had the same wavelength when they leave the laser, after conversion, when they reach the specimen, the beams had different wavelengths. Besides adding cost and complexity to the instrument, some frequency conversion devices are designed to be optimum at just one wavelength, limiting the versatility of the system. Furthermore the techniques require that the focusing optics be achromatized in order to deal with different excitation and quenching wavelengths. Another factor that has impeded the wider adoption of the technique is that because of the complexity of the apparatus to provide two synchronized pulses of different wavelengths to the specimen, the implementations have been in the form of special purpose integrated instruments not well suited to the modular architecture of current scanning microscopes.

OBJECTS AND ADVANTAGES

One object of the present invention is to implement STED and STED-like microscopy or microlithography in which the sculpting beam projected on the specimen has the same wavelength as the excitation beam.

Another object of the invention is to provide a microscope that does not require components for frequency conversion or laser synchronization.

Another object of the invention is to provide a microscope in which only one wavelength of light is required for excitation and quenching, reducing the requirements for chromatic dispersion correction in the focusing optics.

Still another object of the invention is to provide a microscope that can be added in a modular fashion to an existing multiphoton microscope, with large cost savings for an owner of an existing multiphoton microscope.

Still another object of the invention is to provide the resolution advantages of STED and STED-like microscopy, while allowing tuning of the wavelength of excitation, to match the properties of particular fluorophores.

Yet other objects of the invention will become apparent in this disclosure.

SUMMARY OF THE INVENTION

The foregoing objects are achieved and the foregoing problems are solved in one illustrative embodiment of the invention, applied specifically to the field of fluorescence microscopy, although the principles embodied therein also apply to the other applications of the present invention such as microlithography, nanofabrication and optical information storage and retrieval. The specimen to be examined by the microscope is stained with a dye that can be excited to fluorescence via multiple photon absorption at a particular wavelength and where such fluorescence can be quenched by a single photon process by light of this same wavelength. Light from a short pulsed laser such as a mode locked titanium-sapphire laser is split into two portions, one of which is directed to a spot in the specimen as a pulse of no more than a few picoseconds in order to excite the dye at that spot by multiple photon absorption. The second portion of the pulse is stretched to a pulse duration from several to several hundred picoseconds, for example by the well known means of using prisms, diffraction gratings or large pathlengths in dispersive media (eg. in optical fibers) to introduce group velocity dispersion, and this stretched pulse is shaped spatially into a pattern having a point of substantially zero intensity, and imaged on the excited spot following the exciting pulse. By causing this zero intensity point to substantially overlap with the central maximum of the excited spot, and by causing the intensity of the quenching beam to rise quickly with distance from this central point, the quenching thereby increases with distance from the central maximum of the excited spot, reducing its diameter, and thereby increasing resolution. The excited and quenched spot is scanned over the specimen and the fluorescence emanating from the spot, following each quenching pulse, is measured and used to form an image of the specimen, using imaging techniques well know in the art of scanning spot confocal and multiphoton microscopy.

According to one aspect of the invention, an apparatus, for irradiating a selected region of a target material in order to excite members of an excitable species contained within the selected region to a particular state of excitation, includes means for directing to said target material a first radiation and a second radiation. The means for directing the first radiation and the second radiation are configured such that the first radiation is adapted to excite the members to said particular state of excitation, and such that the second radiation is adapted to reduce the ratio of excited members in the particular state of excitation to members not in the particular state of excitation at the selected region. Further, the apparatus provides that the intensity distribution of the first radiation in the target material is significantly different from the intensity distribution of the second radiation. The apparatus includes elements to provide that at the target material, the first and the second radiation have the same wavelength.

According to another aspect of the invention, a method is provided for irradiating a selected region of a target material in order to excite members of an excitable species contained within the selected region to a particular state of excitation. The method includes directing to the target material a first radiation and a second radiation, such that the first radiation is adapted to excite the members to the particular state of excitation and such that the second radiation is adapted to reduce the ratio of excited members in the particular state of excitation to members not in the particular state of excitation at the selected region. Further, the method provides that the intensity distribution of the first radiation in the target material is significantly different from the intensity distribution of the second radiation. The method also causes the first and the second radiation to have the same wavelength at the target material.

BRIEF DESCRIPTION OF THE DRAWINGS

The principles of the invention will be more particularly discussed with reference to the accompanying drawings in which.

DESCRIPTION OF THE INVENTION

Figure 1:
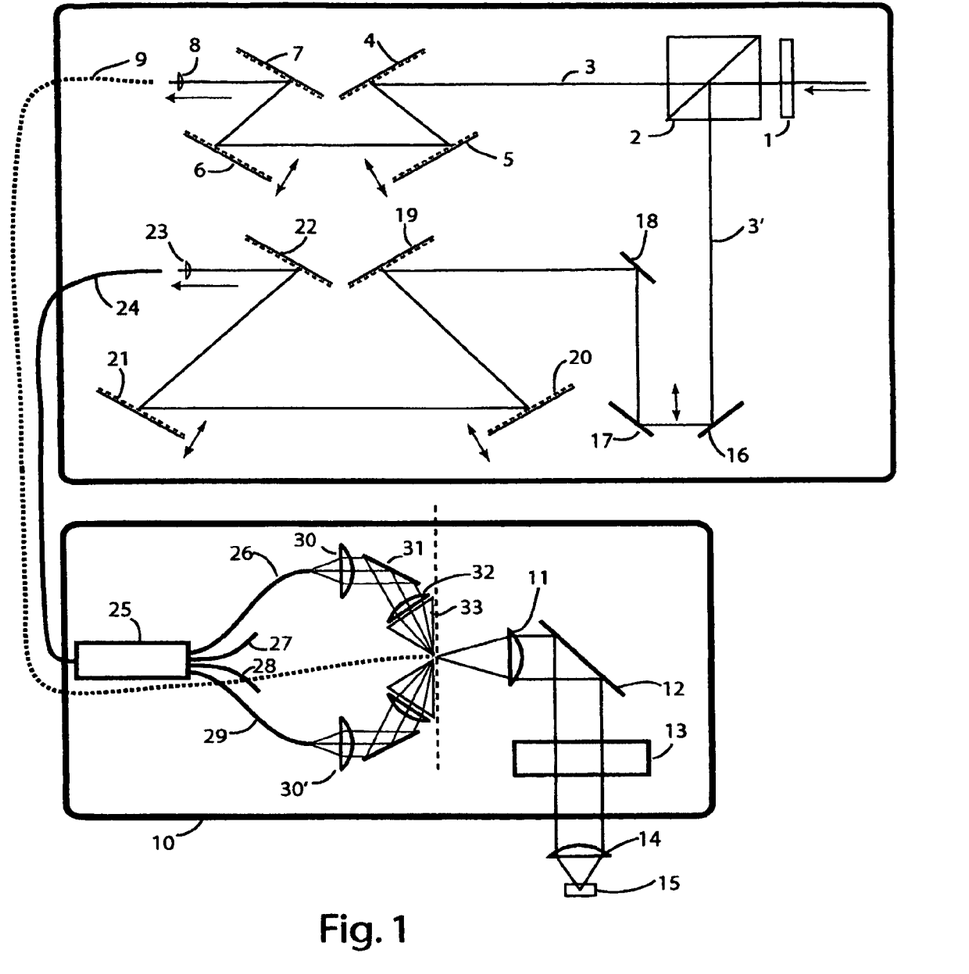
FIG. 1 is a schematic cross-sectional view showing a microscope embodying the invention.

FIG. 1 shows a cross sectional view of an embodiment of the invention for scanned fluorescence microscopy. U.S. Pat. Nos. 5,777,342, 5,866,911, 5,952,668 and 6,259,104 contain useful background to the following discussion, and are incorporated herein by reference. Light from a femtosecond pulsed titanium-sapphire laser is directed on rotatable half-wave plate 1, and the emerging beam is directed onto a polarizing beamsplitter 2. Beam 3, which is one of the beams emerging from the beam splitter 2 will be used for multiphoton excitation. Beam 3 is directed onto a chromatic dispersion compensating assembly, as discussed in U.S. Pat. No. 6,178,041, the disclosures of which are hereby incorporated by reference, consisting of four diffraction gratings 4, 5, 6 and 7. The beam emerging from grating 7 is focused by lens 8 onto one end of an optical fiber 9, which conducts the light to the scan head 10. Negative chromatic dispersion produced by the gratings 4, 5, 6 and 7 compensate for positive dispersion in the fiber 9, so as to maintain a short pulse width in the pulse directed on the specimen, as discussed in U.S. Pat. No. 6,178,041. Within the scan head 10, light leaving the exit end of fiber 9 is collimated by lens 11 and reflected by mirror 12 (which may be a dichroic beam splitter) onto scanning means 13 and then, onto objective 14, which focuses the excitation pulse into a spot in specimen 15.

Beam 3' emerging from beamsplitter 2 will be used to produce the quenching beam. Beam 3' is directed successively to mirrors 16 and 17, the position of which can be moved in the direction of the axis of the beam 3' to induce a variable path length, and thereby change the time delay between the offset of the excitation pulse and the onset of the quenching pulse. The beam emerging from mirror 17 is reflected by mirror 18 to an assembly consisting of four diffraction gratings 19, 20, 21 and 22 that apply negative chromatic dispersion, and the beam emerging from grating 22 is focused by lens 23 onto the end of optical fiber 24. The negative dispersion produced by the assembly of gratings 19, 20, 21 and 22 is greater or smaller than the positive dispersion introduced by fiber 24, so that the pulse experiences a net stretching. As an alternative, the gratings 19, 20, 21 and 22 could be put in a configuration that produces positive dispersion. The stretched pulse conducted by fiber 24 is split by a fiber optical 1:4 splitter 25 equally into four fibers. The light emerging from these fibers 26, 27, 28 and 29 is collimated by four identical lenses, of which only lenses 30 and 30' are in the plane of this drawing and are shown. The beam emerging from lens 30 is reflected by mirror 31 onto lens 32, and the converging beam leaving lens 32 enters equilateral prism 33 where it experiences total internal reflection to be directed parallel to the axis of the cone of excitation light emerging from the end of fiber 9, and it is focused to a spot in the same plane as the end of fiber 9. The ends of fibers 27, 28 and 29 also are focused to spots of light in this same plane, so that the spots are at the corners of a square with the tip of fiber 9 at the center.

Figures 2, 3:
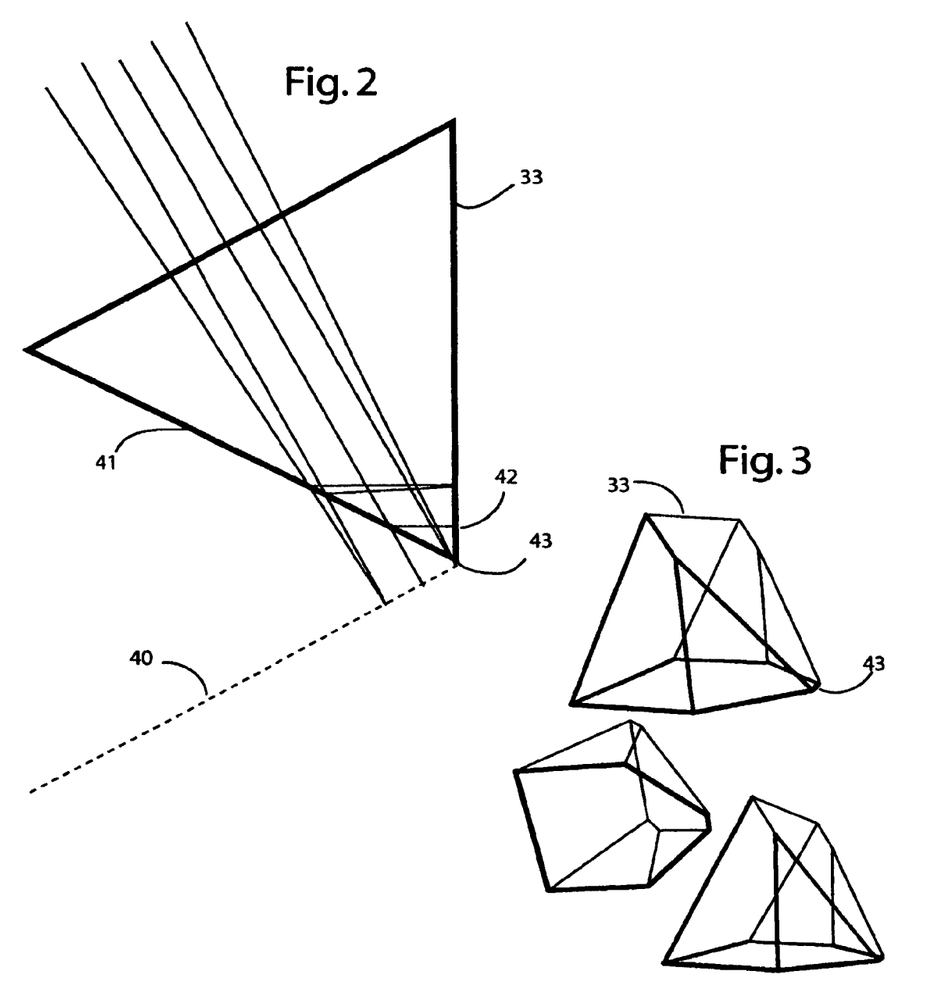
FIG. 2 is a schematic cross-sectional view showing a detail of light rays in a prism shown in FIG. 1.
FIG. 3 is a three dimensional perspective view of three different positions of the prism shown in FIG. 2.

FIG. 2 shows a detail of the passage of rays of quenching light in prism 33. The rays would form an image of the end of fiber 26 at plane 40, but total internal reflection from prism face 41 causes the image instead to be formed at position 42, adjacent to a chisel edge 43 of the prism. FIG. 3 shows a three-dimensional perspective view of different positions of prisms such as prism 33, showing the chisel edge 43. Each of these prisms could be made by placing them so one face is horizontal, and making two cuts at 45° to the edges of the horizontal face, so the cuts almost touch, producing the chisel edge 43.

Figure 4:
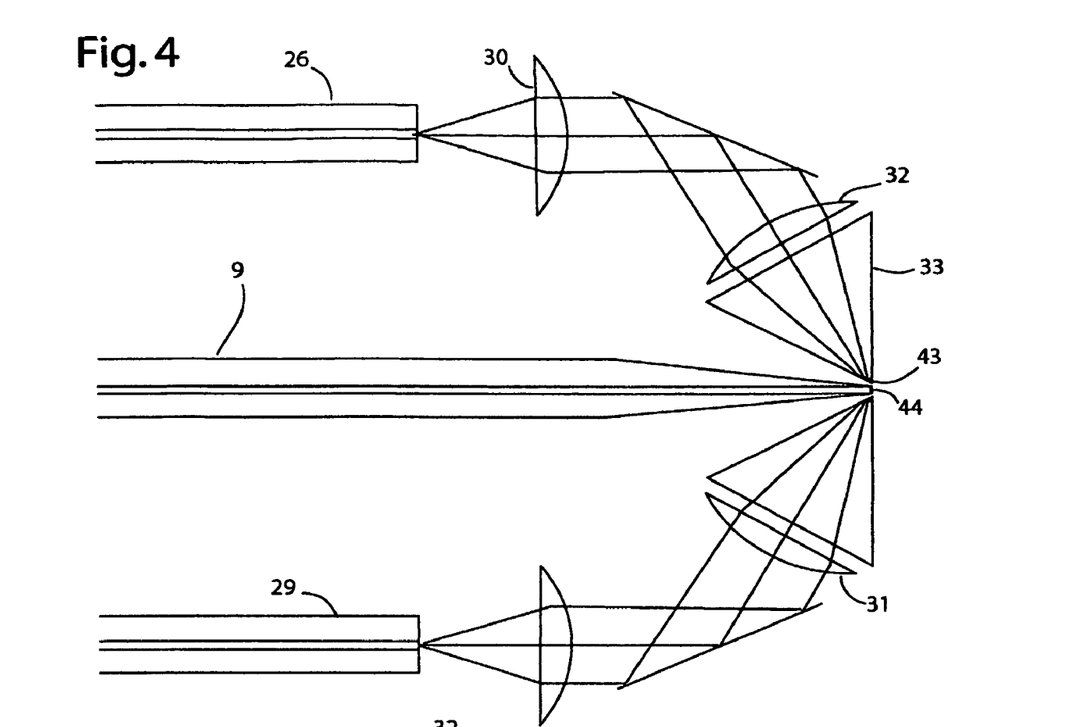
FIG. 4 is a schematic cross-sectional view showing a magnified detail from FIG. 1.
Figure 5:
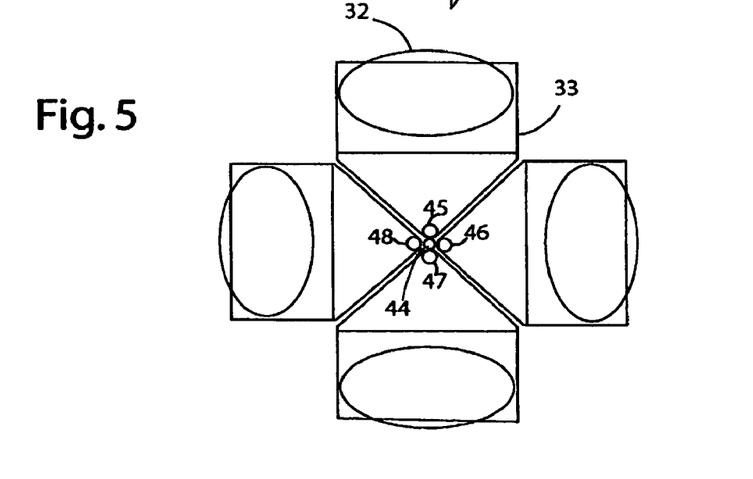
FIG. 5 is a plan view showing the prisms of FIGS. 1, 2, 3, and 4 in which the real image plane is in the plane of the illustration.

When four of such prisms are positioned on a horizontal surface so that these four chisel edges, such as edge 43, make the sides of a square, then they will be in the relative positions required in the device shown in FIG. 1. The magnified detail of FIG. 1 shown in FIG. 4, shows how the end of fiber 9 can be tapered, by gradually removing the cladding, so at the tip only the core plus the minimum cladding needed to maintain propagation remains, and this tip just fits into this square, the edges of which are the chisel edges, such as edge 43. FIG. 5, shows a plan view, such that the plane of the figure is parallel to the real image plane containing the tip 44 of fiber 9, and the spot images 45, 46, 47 and 48 of the ends of fibers 26, 27, 28 and 29. FIG. 5 shows the relationship between these spot images and the tip of excitation fiber 9.

Lenses 11 and 13 and mirror 12 reimage these spot images 45, 46, 47 and 48 to the real image plane of the specimen 15, such that these reimaged spot images in the specimen are at the corners of a square. The reimaged spots diagonally opposite each other have a 180° phase difference, so that the light exactly cancels at the central point of the square, which is also the central point that the tip of fiber 9 that is imaged to in the specimen. This phase adjustment can be made, for example, by axially moving fiber 26 with respect to fiber 29, until the desired cancellation is produced. As discussed in the cited references, it is important that light from one pair of diagonally opposite reimaged spot images does not interfere with light from the remaining pair. One way that this can be accomplished, as discussed for example in U.S. Pat. No. 6,259,104, is to make the phase relationship between adjacent pairs of reimaged spot images have a 90° phase difference, and again the required phase relationships can be produced by axially moving the tips of the fibers 26, 27, 28 and 29 relative to each other. The resulting phase can be described as adding 90° of phase shift as one moves clockwise in the plane of focus of the specimen from each of the four reimaged spot images to the next one. The cited references describe other ways of providing that light from opposite reimaged spot images cancels but light from one of these opposite pairs cannot interfere with light from the remaining pair.

The dimensions are chosen so that the distance between the centers of the reimaged spot images and the center of the image in the specimen of the tip of fiber 9 is about 2.3 dimensionless optical units (a separation of one optical unit equals the inverse of the product of numerical aperture of the objective lens and the wavevector $k=2\pi/\lambda$). This geometry will produce a doughnut shaped intensity distribution in the real image plane of the specimen, with a theoretically zero intensity central spot, and where the intensity rises rapidly with distance from that central point.

The styryl dye RH414 appears suitable for multiphoton excitation and for quenching at the same wavelength, in this case 760 nm. The paper by Dyba and Hell (Appl. Optics. 42:5123 (03)) shows that light of this wavelength will lead to multiphoton fluorescent excitation. An earlier paper by the same authors (Phys. Rev. Lett. 88:163902 (02)) showed that the same dye was susceptible to STED quenching by light around the same wavelength. There are other possible candidate dyes including DiD, and it appears possible that the ability to be multiphoton excited and quenched by light of the same wavelength will turn out to be a relatively common property of dyes, not presently known only because it has not been looked for.

The above discussion has not dealt with the issues of measurement of light emitting from the excited spot, and creation of an image based on scanning of the excited spot. That is because the process is the same as in well known confocal (eg. Baer, U.S. Pat. No. 3,705,755), multiphoton (eg. Denk et al, U.S. Pat. No. 5,034,613, the disclosures of which are hereby incorporated by reference) and the already cited STED patents. As in multiphoton and STED imaging, the light emanating from the excited spot can either be descanned and imaged on a confocal pinhole, or imaged on a detector without descanning or passage through a confocal pinhole, for greater collection efficiency.

Many alternative methods have been described for producing a sculpting beam with the required zero intensity central point (or line, in the case of line scanning microscopes) and any of these could be applied to the present invention, provided the wavelength of the sculpting beam was the same as the excitation wavelength. Although the preceding description described a fiber to couple the excitation laser to the microscope scan head, the present invention would also be applicable in instruments where the path between the laser and the scan head did not involve passage through an optical fiber.

The same principle of multiphoton excitation and quenching by a lengthened pulse of the same wavelength could be used for scanned beam microlithography and microfabrication. For microlithography, the goal is to quench the peripheral parts of an excited spot in the photosensitive film or emulsion layer, before they have lead to the lasting change. The two-photon-activatable photoacid generator molecule, $BSB-S_2$, has been used for two-photon microfabrication (Zhou et al Science 296: 1106(02)) using light of 705 to 800 nm. This substance also has a relatively long lived singlet state that might be susceptible to single-photon-induced quenching in this general wavelength range, and also has a sufficiently long lived excited singlet state, that quenching should be possible before the acid triggering the lasting change is released.

Figure 6:
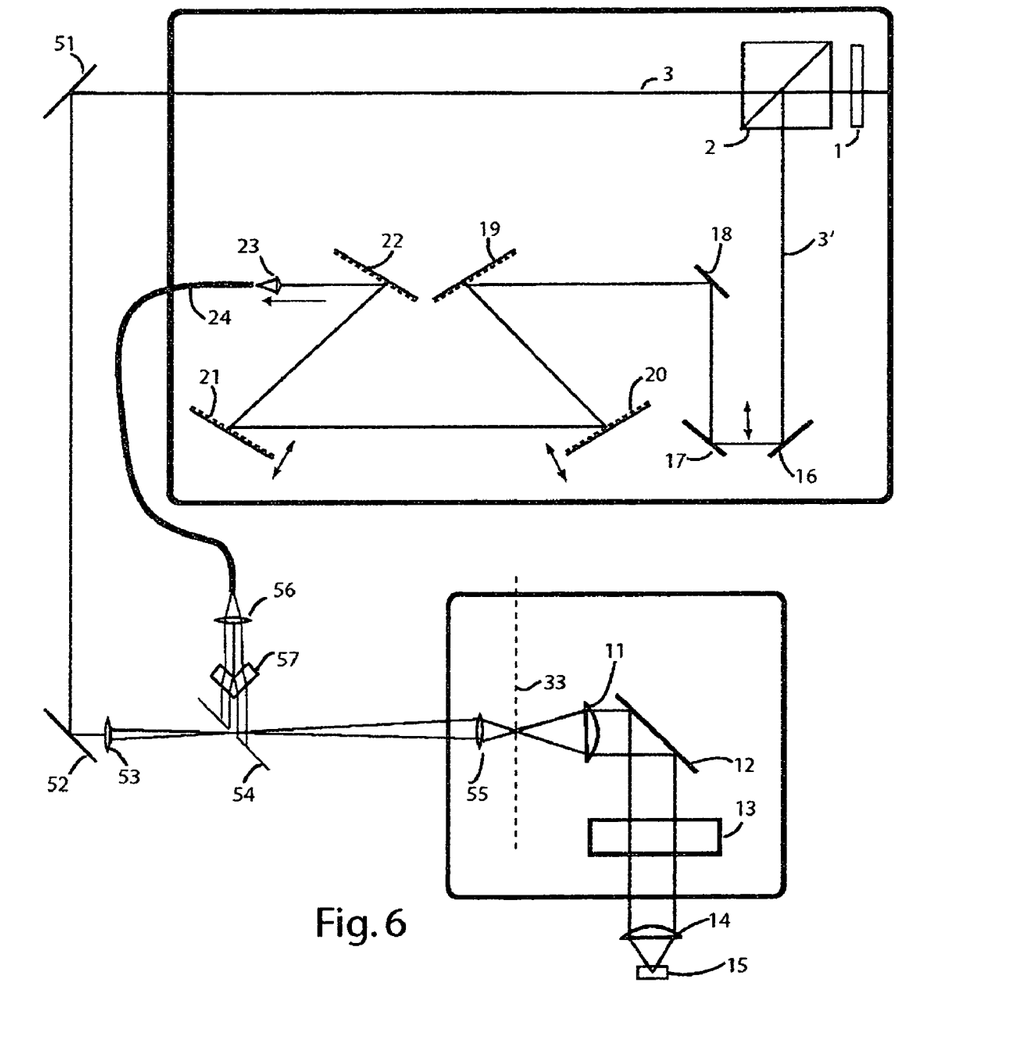
FIG. 6 is a schematic cross-sectional view showing an embodiment of the instrument.

The device of FIG. 1 allows a common wavelength to be used both for excitation and for reducing the excitation in the peripheral parts of the excited spot or line. However because the axial positions of the fibers 26, 27, 28 and 29 must be adjusted to create phase differences of 90°, 180°, and 270° and because the particular distance to create these phases is proportional to the wavelength, the fibers must be repositioned whenever that common wavelength is changed. The device shown in FIG. 6 creates phase differences that do not require mechanical readjustment when the wavelength is changed, and for that reason is a more preferred embodiment of the present invention. Those elements in FIG. 6 that are identical to elements in FIG. 1 have been given the same reference numerals. There are some differences. For example, in FIG. 1, the transmitted component 3 from beam splitter was passed through a chromatic dispersion means and then conducted by an optical fiber in its passage to the scan head 10. In the device of FIG. 6, in contrast, there is no intervening optical fiber, and consequently there is no need for the chromatic dispersion means which is required in the FIG. 1 device to compensate for the opposite chromatic dispersion of the fiber, to maintain the short excitation pulse width. The excitation beam instead is conducted by mirrors 51 and 52, passed through a small transparent hole in segmented mirror 54, which will be explained more fully in the next paragraph, and focused by lenses 53 and 55 onto the real image plane 33. The system of conduction by a fiber and compensation by a chromatic dispersion means, as shown in FIG. 1, has reportedly been found to be difficult to adjust, and so a light conduction method such as shown in FIG. 6, avoiding such a fiber would probably be preferable in a system where the common wavelength is adjustable.

Figures 7, 8, 9:
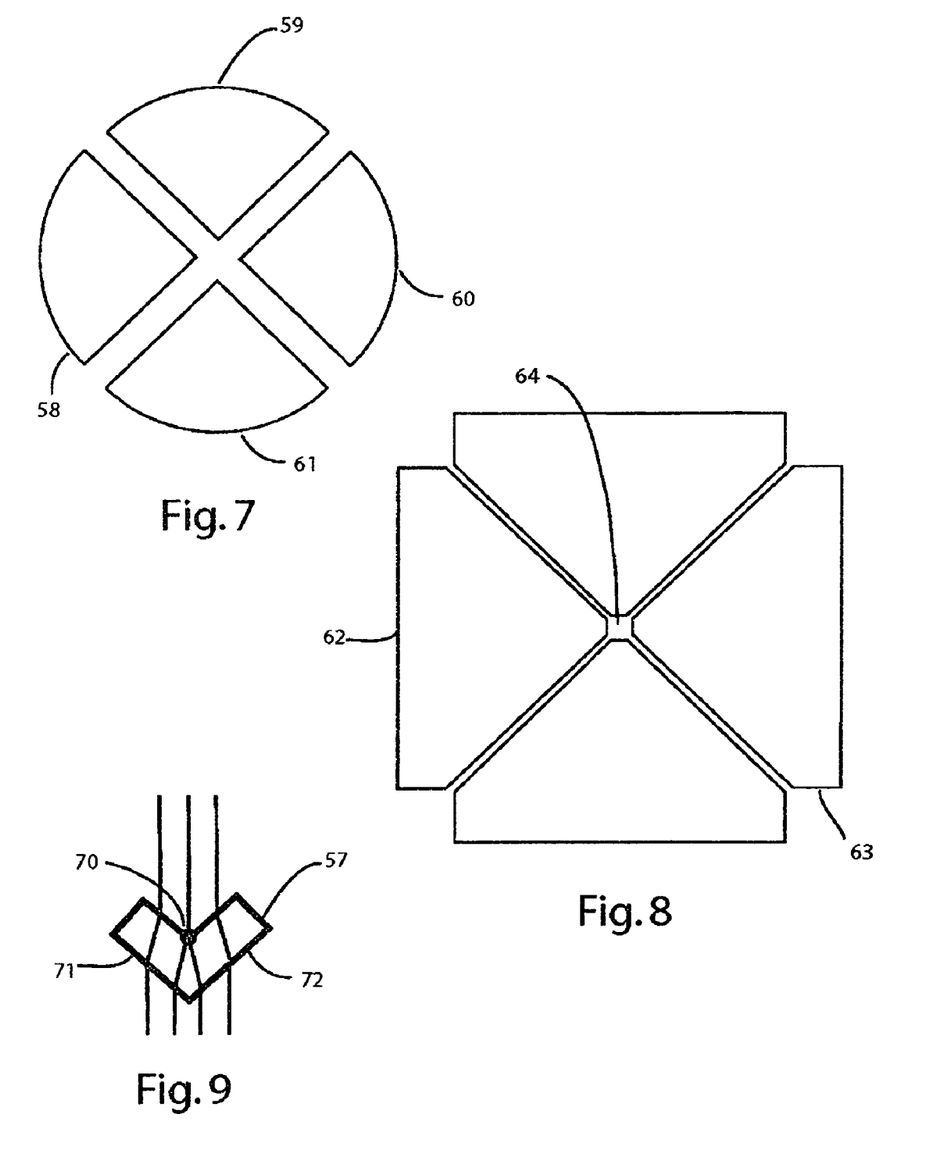
FIG. 7 is a schematic cross-sectional view of the four beam segments emanating from the hollow pyramid illustrated in the device of FIG. 6.
FIG. 8 is a plan view of the segmented mirror in the device illustrated in the device of FIG. 6.
FIG. 9 is a magnified cross-sectional view of the hollow pyramid illustrated in the device of FIG. 6.

The excitation-reducing beam in the FIG. 6 device, which as in the FIG. 1 device is formed from the reflected output 3' from beam splitter 2, is passed through the same chromatic dispersion means and optical fiber as in the FIG. 1 device. After collimation by lens 56, the beam is directed onto a hollow pyramid 57, which separates the beam into four quarter-pie-shaped segments, 58, 59, 60 and 61, separated by a non-illuminated x-shaped region, as shown in FIG. 7. Pyramid 57 is made of four triangles of a transparent material such as glass, with parallel faces, and edges beveled to fill the space at edges where the triangles touch. The cross-sectional plane of FIG. 6 bisects two opposite triangles of pyramid 57

Each of the pie-shaped segments of the beam is directed to a separate segment of segmented mirror 54, shown schematically in FIG. 8, with an exaggerated spacing between the segments. The central hole 64 of the segmented mirror is formed by making a small bevel at the right angle vertices of each of the four mirror segments. Beam segment 58 for example would be directed on mirror segment 62 and beam segment 60 would be directed on mirror segment 63. The segmented mirror 54 reflects the beam segments onto lens 55, which forms a real image of the segmented mirror and its central hole on real image plane 33. Therefore an image of the central spot of the excitation beam is formed at plane 33, surrounded by images of the four beam segments. FIG. 6 is meant to show the relationship between the elements but not their relative sizes. The elements should be arranged so that the images in the plane of focus of the specimen of the "intensity-weighted central point" of the beam segments at plane 33 are about 2.3 optical units from the center of the excitation spot. The "intensity-weighted central point," roughly speaking, would be the center of mass of a flat piece of pie that had a mass per unit area at each point proportional to the light intensity of the pie shaped segment.

As shown in FIG. 9, which is a magnified detail of FIG. 6 to better show pyramid 57, the pyramid can rotate about a point 70, which is the interior vertex point. Pyramid 57 can rotate through small angles on two perpendicular axes of rotation, both of them perpendicular to the optical axis, and one of them perpendicular to the plane of FIGS. 6 and 9. It will be appreciated from FIG. 9 that if the pyramid rotates a small angle on the axis perpendicular to the figure, that the angle of incidence of the collimated beam from lens 56 will increase on one pyramid face and decrease on other. Because of Snell's law, the angle of refraction will also change, so that after the rotation, the distance the beam travels through the glass of face 71 will be different from the distance the opposite beam travels through face 72, which will create a phase difference between the beams, that increases with the tilt of the pyramid.

For any chosen phase difference, for example the 180° phase difference required for the spots of excitation-reducing light on opposite sides of the central spot of excitation, and for any chosen wavelength, whatever relative delay between the opposite faces that is produced by tilting of the pyramid to an arbitrary angle, there is a compensatory translation of the segments of segmented mirror, that when combined with the delay caused by mirror rotation (which at a very small angle approximates translation), will restore the net delay to create a 180° phase difference. It is possible to imagine a graph where the relative delay caused by the pyramid tilt is plotted on one axis and the compensatory movement of the mirror segments to make the net phase difference 180° is plotted on the other axis. The resulting graph will be a sloping line. A change of wavelength of the beam will change the speed of light through the glass, and consequently change the slope such a plotted line. Because they have different slopes, the lines corresponding to two chosen wavelengths will intersect at some point. The coordinates of this intersection point indicates a pair of relative delays caused by pyramid tilt and by mirror segment adjustment, such that the net delay is 180° for both of these wavelengths. If the pyramid is tilted at the angle needed to produce such a delay and the mirror segments are set at the corresponding positions, not only will the phase delay be exactly 180° for both of the chosen wavelengths (which are chosen to bracket the wavelength band desired for the quenching light), but additionally it will be nearly 180° for all the wavelengths in between. This is the well-known principle of achromatic correction, and it is particularly simple to implement in this case. The result is that not only is the arrangement of FIG. 6 simpler than the arrangement of FIG. 1, but it also is substantially achromatic for phase delay.

It should be understood that to calibrate this system, three separate degrees of freedom are required to produce the required phase delays, but rotation of the pyramid only provides two such degrees of freedom. One possible solution is to cement three of the four triangular faces together, and allow the fourth face to pivot about the common vertex point 70. It is possible to perform such a calibration of the delays during fabrication of the pyramid, and then in use, the two available degrees of freedom could be used for fine adjustment.

In addition to allowing the common wavelength to be changed without need to recalibrate the phase adjustments, an achromatic scheme also insures that when the pulses are spectrally broadened as a side effect of pulse compression and stretching, that each spectral component in the broadened pulse has the same phase delay, and as a consequence they each form a zero intensity point at the central point. Even in a fixed wavelength instrument, this may contribute to a slight improvement in resolution.

Although this disclosure has described single wavelength STED microscopy with just one illustrative STED microscope design, it will be obvious to one skilled in the art that provided a suitable fluorophore or photosensitizer is used, that the present invention could be applied to nearly any of the many other designs for STED and STED-like microscopes or microlithography exposure tools described in the cited references, including but not limited to devices with multiple simultaneously imaged spots, and a line-shaped rather than spot-shaped area subject to resolution enhancement, and to devices still to be proposed. The breadth of the present invention should not be limited by the particular illustrative examples but rather by the following claims.

What is claimed is:

1. An apparatus for irradiating a selected region of a target material in order to excite members of an excitable species contained within said selected region to a particular state of excitation to produce a measurable effect, comprising:

an excitable species within said target material adapted to undergo excitation to said particular state of excitation when excited by brief pulses of radiation of a particular wavelength, to produce said measurable effect, and wherein, when said region is irradiated by longer pulses of said radiation of said particular wavelength, said measurable effect in response to said brief pulses is reduced;

a source of radiation producing pulses sufficiently brief to excite said species, apparatus to split the radiation emanating from said source into a first beam of radiation and a second beam of radiation;

a pulse stretcher in the path of said first beam adapted to increase the duration of pulses entering it;

a pulse shaper in the path of said first beam, such that on emerging from said pulse shaper said first beam has a direction of propagation and a cross section perpendicular to said direction of propagation, and such that there is at least one minimum in the intensity of radiation of said beam in said cross section; and a beam combiner to combine first beam, after passing through both said pulse stretcher and said pulse shaper, with said second beam, to form a combined beam, directed to said material.

2. The apparatus of claim 1, wherein said long pulses the duration of which was increased by passing through said pulse stretcher quench excitation in said species.

3. The apparatus of claim 1, wherein said radiation arriving at said beam combiner contains no radiation not originally produced in said source.

4. The apparatus of claim 1, wherein the radiation arriving at said beam combiner in said brief pulses and said pulses the during of which is increased by said pulse stretcher have substantially the same spectral content.

5. The apparatus of claim 4, wherein said spectral content contains a dominant wavelength.

6. The apparatus of claim 1, wherein the longer duration pulses from said first beam arrive at said beam combiner after said brief pulses from said second beam arrive there, so that in said material said longer duration pulses follow said brief pulses.

7. The apparatus of claim 1, wherein the measurable effect is the production of measurable light upon excitation, and the result of the long pulses is to reduce the light so measured.

8. The apparatus of claim 1, wherein said material is a photolithographic emulsion and the measurable effect is the production of a lasting change in said emulsion, for the purpose of creating a photolithographic image or forming an nanofabricated object.

9. The apparatus of claim 1, wherein said the radiation from said second beam converges to a spot in said material and the radiation from said first beam is focused to a pattern having a minimum substantially coincident with said spot.

10. The apparatus of claim 9, wherein the intensity of said light from said second beam at the central point of said minimum is substantially zero.

11. The apparatus of claim 1 wherein said second radiation is focused to a line in said material.

12. The apparatus of claim 1 wherein the radiation in said first and second beams has substantially the same wavelength.

13. The apparatus of claim 1, wherein said the radiation from said second beam converges to a spot in said material and the radiation from said first beam is focused to a pattern having a minimum substantially coincident with said spot.

14. The apparatus of claim 13, wherein the intensity of said light from said second beam at the central point of said minimum is substantially zero.

15. A method for irradiating a selected region of a target material in order to excite members of an excitable species contained within said selected region to a particular state of excitation to produce a measurable effect, comprising the steps:

providing an excitable species within said target material adapted to undergo excitation to said particular state of excitation when excited by brief pulses of radiation of a particular wavelength, to produce said measurable effect, and wherein when said region is irradiated by longer pulses of said radiation of said particular wavelength, said measurable effect in response to said brief pulses is reduced;

providing a source of radiation producing pulses sufficiently brief to excite said species;

splitting the radiation emanating from said source into a first beam of radiation and a second beam of radiation;

stretching the pulses in said first beam to increase their duration of pulses;

shaping the radiation in said first beam, to create a beam with at least one minimum;

combining said first beam, after it has been transformed by the steps of pulse stretching and shaping, with said second beam, to make a combined beam; and directing said combined beam to said material.

16. The method of claim 15, comprising the additional step of quenching said state of excitation by the stretched pulses of said first beam.

17. The method of claim 15 wherein said step of directing said combined beam to said material is such that the said brief pulses in said second beam arrive at said material prior to the stretched pulses of said first beam.

18. The method of claim 15 wherein all of the radiation in said combined beam was produced in said source.

19. The method of claim 15 wherein the component of said combined beam containing the radiation from said first beam has substantially the same spectral content as the component of said combined beam containing the radiation from said second beam.

20. The method of claim 15 wherein the component of said combined beam containing the radiation from said first beam has a dominant wavelength the component of said combined beam containing the radiation from said second beam has a dominant wavelength, such that said dominant wavelengths in said first and second beam are substantially identical.

21. The method of claim 15, wherein said material is a photolithographic emulsion and the measurable effect is the production of a lasting change in said emulsion, for the purpose of creating a photolithographic image or forming an nanofabricated object.

22. The method of claim 15 wherein said second radiation is focused to a line in said material.

23. The method of claim 15 wherein the radiation in said first and second beams has substantially the same wavelength.

* * * * *